United States Patent [19]
Nicolais et al.

[11] Patent Number: 5,645,592
[45] Date of Patent: Jul. 8, 1997

[54] USE OF HYDROGELS TO FIX BONE REPLACEMENTS

[75] Inventors: Luigi Nicolais, Ercolano; Luigi Ambrosio, Ottaviano; Paolo Antonio Netti, S. Gennaro Vesuviano; Lanfranco Callegaro, Ponte di Brenta, all of Italy

[73] Assignee: M.U.R.S.T. Italian Ministry for Universities and Scientific and Technological Research, Rome, Italy

[21] Appl. No.: 341,541

[22] PCT Filed: May 21, 1993

[86] PCT No.: PCT/EP93/01288

§ 371 Date: Apr. 27, 1995

§ 102(e) Date: Apr. 27, 1995

[87] PCT Pub. No.: WO93/23094

PCT Pub. Date: Nov. 25, 1993

[30] Foreign Application Priority Data

May 20, 1992 [IT] Italy ................... PD92A0088

[51] Int. Cl.$^6$ ................................... A61F 2/28
[52] U.S. Cl. .................. 623/16; 606/76; 606/63; 623/901
[58] Field of Search ................. 623/16; 606/63, 606/66, 68, 71, 70, 76; 604/266

[56] References Cited

U.S. PATENT DOCUMENTS

| | | | |
|---|---|---|---|
| 4,487,865 | 12/1984 | Balazs et al. | 524/29 |
| 4,527,293 | 7/1985 | Eckstein et al. | 623/12 |
| 4,863,444 | 9/1989 | Blömer | 606/76 |
| 5,084,050 | 1/1992 | Draenert | 606/63 |
| 5,329,846 | 7/1994 | Bonutti | 623/901 |
| 5,439,684 | 8/1995 | Prewett et al. | 623/16 |

*Primary Examiner*—Paul B. Prebilic
*Attorney, Agent, or Firm*—Birch, Stewart, Kolasch & Birch, LLP

[57] ABSTRACT

Provided are orthopedic fasteners and replacements such as nails, screws, pins, hip and knee replacements, etc., coated with hydrogels and other biocompatible/biodegradable materials which expand in the presence of liquids. Swelling of such coatings causes the fastener or replacement to be securely fixed into position once inserted into bone material. Useful coating materials include methacrylates, hyaluronic acid esters, and crosslinked esters of hyaluronic acid resulting from the esterification of hyaluronic acid with polyhydric alcohols. Also provided is a method for fixing a bone or bone replacement in position employing such coated orthopedic fasteners or replacements.

26 Claims, 5 Drawing Sheets

USE OF HYDROGELS TO FIX BONE REPLACEMENTS

BACKGROUND OF THE INVENTION

1. Field of the Invention

The present invention relates to the coating of orthopedic replacements such as intramedullary nails, screws, hip replacements, etc., with hydrogels and other biocompatible/biodegradable materials which expand in the presence of liquids. Expansion of the outer coating causes the replacement to be fixed into position once inserted into the intramedullary bone cavity. The same principle applies in the case of similarly coated screws and nails, which are thus able to maintain their mechanical hold where they are inserted in intracortical holes, and improve the function of normal spiral screws. Coating can be done by direct polymerization of the monomer by immersion in the case of coatings made with linear polymers. The degree of pressure exercised after expansion is controlled by the degree of cross-linking of the polymeric network, by the thickness of the coating, and by the presence of organic or inorganic inclusions in the coating.

2. Description of Related Art

Current treatments for bone fractures involve the use of stiff plates which lend mechanical support to the join until the tissues have had time to heal. The plates are fixed to the bone by spiral screws screwed into the bone itself (Amis et al.: Fatigue fracture of a femoral sliding compression screw-plate device after bone union. *Biomaterials*, Vol. 8, 1987). As the plate is stiffer than the bone, it bears most of the strain inflicted on them, whereby the bone is actually protected from any strain. This protection results in anomalous regrowth of the natural tissue and prevents the early mending of the bone parts because of the formation of callus during the process of reconnection (Szivek et al.: A study of bone remodelling using metal-polymer laminates. *J. of Biomedical Materials Research*, Vol. 15, 853–865, 1981). Over time, the extreme stiffness of the plate can cause atrophy and osteoporosis.

Another problem arises from the type of fastener used to fix the plate to the bone. These are usually metal screws driven directly into the bone, and often cause local trauma by tearing the tissues holding the screw. This often causes inflammation and further problems connected with the healing of the tear.

The most widely used cements are based on acrylates, e.g., PMMA, in the monomeric or mixed monomeric-polymeric phase which are then polymerized in vivo (M. F. Refojo: Materials for use in the eye, in *Polymers in Medicine and Surgery*, R. L. Kronenthal et al., eds. Plenum Press, New York, Vol. 8, page 313, 1975). Direct polymerization gives rise to a series of disadvantages essentially linked to the difficulty of controlling the reaction from the outside (W. Petty: Methyl methacrylate concentrations in tissues adjacent to bone cement. *J. of Biomedical Materials Res.*, Vol. 14, 427–434, 1980). The exothermic character of the polymerization reaction causes the formation of hot spots reaching unbearably high temperatures for the surrounding tissues, which consequently become degraded (Kliment et al.: Use of spongy hydron in plastic surgery. *J. Biomed. Mater. Res.*, Vol. 2, 237, 1968). In order to avoid this degradation, the reaction is made as mild as possible, but this in turn decreases the degree of conversion with a consequent increase in the percentage of unreacted products which cannot be eliminated (Willert et al.: Measurements of the quantity of monomer leaching out of acrylic bone cement into the surrounding tissues during the process of polymerization. *Biomedical Applications Of Polymers*, H. P. Gregor, ed., Plenum Press, 1975). The absorption of unreacted acrylic monomers is a highly toxic phenomenon, and can lead to very serious consequences (Silvestre et al.: Failure of acrylic bone cements under triaxial stresses. *J. of Materials Science*, Vol. 25, 1050–1057, 1990).

Furthermore, in the last few years, medical research has disclosed that the pathology of articular arthrosis is also occurring in younger patients (S. Spainer: Histology and Pathology of Total Joint Replacement, in *Total Joint Replacement*, chapt. 7, pp. 61–74, William Petty, ed., W. B. Saunders Company, 1991). This, coupled with the extension of the average life, often requires more than one operation. The actual technique for the hip prosthesis cementation does not permit, because of the irreversibility of the polymerization, easy re-operation of the patient.

Hydrogels are a broad class of polymeric materials which swell extensively, but do not dissolve in water. They include many natural materials of both plant and animal origin. As a result of the similarities between synthetic and natural hydrogels, these gels have been used in a wide variety and growing number of biomedical applications such as opthamology (M. F. Refojo, "Materials for Use in the Eye", in *Polymers in Medicine and Surgery*, R. L. Krunenenthal et al., eds., Plenum Press, New York and London, Vol. 8, 313, 1975), plastic surgery (Kliment et al., "Use of Spongy Hydron in Plastic Surgery", *J. Biomed. Mater Res.*, Vol. 2, 237, 1968), orthopedics (Migliaresi et al., "Hydrogels for Artificial Tendons," in *Hydrogels in Medicine and Pharmacy*, Vol. III, chapt. 4, page 83, N. A. Peppas, ed., CRC Press, 1987), pharmacy (N. A. Peppas, "Release of Bioactive Agents from Swellable Polymers: Theory and Experiments", in *Recent Advances in Drug Delivery Systems*, Anderson et al., eds., Plenum Press, New York, 279, 1984), as well as medical devices (Kocvara et al., "Gel-Fabric Prostheses of the Ureter," *J. Biomed. Res*, Vol. 1, 325, 1967) and other related applications (Rather et al., "Hydrogels for Medical and Related Application", J. Andrate, ed., ACS Symposium, Washington, D.C., chapt. 1, 1976); N. A. Peppas, "Other Biomedical Applications of Hydrogels," in *Hydrogels in Medicine and Pharmacy*, Vol. III, chapt 9, page 177, N. A. Peppas, ed., CRC Press, 1987).

Hydrogels are three-dimensional polymeric networks held together by crosslinks of either weak cohesive forces, hydrogen bonds, or ionic bonds. These networks imbibe large quantities of water (or organic liquids) without dissolution.

The ability of natural tissues to grow into the hydrogel matrices makes them very attractive for biomedical uses (P. A. Davis, PhD Thesis, "A Biodegradable Artificial Composite Tendon Prosthesis", University of Connecticut, 1990, Chapt. 2, pages 46–68; Kobelar et al.: "Experimental Implantation of Hydrogels into Bone", *J. Biomed. Mater. Res.*, Vol. 22, 751, 1988). This and other attributes, such as permeability to small molecules, e.g., metabolites, a soft consistency, and a low interfacial tension between the gel and aqueous solutions are some of the important properties which have generated interest in hydrogels as useful biomaterials. Moreover, the ease of purification, adjustable mechanical properties, and high equilibrium water content, along with their sterilizability, makes these materials ideal for biomedical use.

The simultaneous presence of hydrophilic and hydrophobic groups in the complex structure of the polymeric network is responsible for the expansion of these materials in the presence of water or other polar solvents. When wet, hydrogels have a soft consistency similar to that of natural soft tissues (Hoffman A. S.: Hydrogels—a broad class of biomaterials, in *Polymers in Medicine and Surgery*, R. L. Kronenthal et al., eds., Plenum Press, New York, 1975). The enormous interest in these materials is mainly due to their high biocompatibility (Korbelar et al.: Experimental implantation of hydrogel into the bone. *J. of Biomedical Materials Research*, Vol. 22, 751–762, 1988). Initially used to make contact lenses, hydrogels are today applied in various areas of medicine and pharmacy.

SUMMARY OF THE INVENTION

The present invention offers a remedy to a whole series of problems connected with the use of bone cements commonly used in orthopedics to fix intramedullar nails, such as in the case of substitution of the top of the femur in hip replacement operations. It also offers an alternative to current techniques by avoiding many of the problems noted above. Hydrogel coatings on nails, screws, joint replacements such as for the hip and knee, etc., which are fixed in position by intramedullary cementing, make possible a whole series of improvements in the field of orthopedic replacements.

The use of intramedullary nails coated with hydrogels can guarantee the mechanical hold of the fracture, owing to the stress exerted by the coating material on the bone surface while absorbing liquid without swelling. In this way, the soft consistency of the bone-hydrogel interface can prevent anomalous fracture healing (osteoporosis) frequently observed with currently used replacements. Fractures are fixed in this way by a system of radical stress generated by the coating that presses against the cortical wall of the bone and guarantees a firm mechanical hold.

The bone is not, therefore, protected from stress, but will almost completely bear the axial component of the weight pressing on it. Joining of the fracture will in this way be quick and free from primary callus formation.

The use of coated intracortical screws allows a firm mechanical hold and at the same time avoids problems caused by normal spiral screws. The anomalous distribution of stress is avoided by the soft consistency of the coating material, which allows the stress to be distributed uniformly.

The idea of replacing commonly used bone cements is to provide a hydrogel coating on the part of the replacement which is to be inserted intramedullarly, with subsequent expansion due to the absorption of liquids by the coating, ensuring the tight hold of the replacement. For example, when replacing the top of the femur, a hydrogel coating on the stem of the replacement will eliminate the need for cement, and consequently the problems caused by in vivo polymerization. All materials currently used in the field of orthopedic replacements can be thus coated, even those made of stainless steel, metal alloys, titanium, or cobalt-chromium, following treatment of the surfaces to improve metal-polymer adhesion.

The coating of intracortical screws or intramedullar nails is effected with specially made teflon moulds into which the monomeric mixture is injected. The polymerization is conducted at a suitable temperature according to the degree of cross-linking desired in each particular case (Nicolais et al.: Mechanical behavior of poly(2-hydroxy-ethylmethacrylate) glass bead composites, in *Chemistry and Properties of Crosslinked Polymers*, S. S. Labana, ed., Academic Press Inc., 1977; Davis et al.: Poly(2-hydroxyethyl methacrylate) /Poly(caprolactone) Semi-interpenetrating Polymer Networks, *J. of Bioactive and Compatible Polymers*, Vol. 3, 205–218, July 1988; Davis et al.: Modified PHEMA Hydrogels, in *High Performance Biomaterials*, M. Szycher, ed., Technomic Publ., 1991).

After polymerization, the system is immersed in water where expansion of the hydrogel disposes of unreacted monomers. Subsequent drying and sterilization by beta rays produces the ready-to-use manufact.

The present invention has many applications. The coatings can be prepared with various materials and by various processes as long as they possess the above-said characteristics.

Accordingly, it is an object of the present invention to provide an orthopedic fastener or replacement, covered with a coating comprising a hydrogel or other biocompatible, biodegradable material which expands in the presence of a liquid.

It is another object of the present invention to provide a method for fixing a bone or bone replacement in position, comprising the steps of:

(a) providing a hole in existing bone to accommodate a fastener;

(b) locating a bone or bone replacement adjacent to said existing bone, said bone or bone replacement having a hole therein to accommodate a fastener;

(c) providing a fastener according to claim 1; and (d) inserting said fastener of step (c) into the holes in said existing bone and said bone or bone replacement such that said coating absorbs fluid and swells, thereby securely fixing said bone or bone replacement in position.

Further scope of the applicability of the present invention will become apparent from the detailed description and drawings provided below. However, should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention, in which.

DETAILED DESCRIPTION OF THE INVENTION

The following detailed description of the invention is provided to aid those skilled in the art in practicing the same. Even so, the following detailed description should not be construed to unduly limit the present invention, as modifications and variations in the embodiments herein discussed may be made by those of ordinary skill in the art without departing from the spirit or scope of the present inventive discovery.

The contents of each of the references cited in the present disclosure are herein incorporated by reference in their entirety.

To illustrate some possible preparative methodologies, reported hereafter are practical examples which are not, however, to be considered exhaustive.

To verify possible applications of the invention, various tests have been carried out to assess the extent of stress which the system is able to bear and the kinetics by which it does so as the hydrogel expands. These tests consist of measuring the force required to extract a coated nail from its socket once it has reached a steady state of water absorption.

EXAMPLE 1

Stainless steel orthopedic nails measuring 2.5 mm in diameter and 30 mm in length were coated with polyhydroxyethylmethacrylate (PHEMA) at coating thicknesses of 0.5, 1, 1.5 and 2 mm. Coating was carried out by means of a PTFE mould, designed to produce a centered coating onto the pins. The reactive solution of monomer (HEMA) was prepared according to the Witchterle and Lim procedure (O. Witchterle, D. Lim, "Hydrophilic Gels for Biological Use", *Nature* (London) 185:117, 1960). EDMA (ethylene-dimethacrylate) was used as the crosslinking agent, and AIBN (azobisisobutyronitrile) as the initiator, in a weight percentage of 0.5% and 0.1%, respectively. The coated specimens were obtained by injecting the reactive solution into the mould and letting it polymerize in an oven at 80° C. for two hours. The coated pins so obtained were placed in a ceramic material with a porosity similar to that of bone. The dimensions of the holes made in the material were the same as those of the external diameter of the coated pins. The whole system was placed in distilled water for 48 hours.

Figure 1:
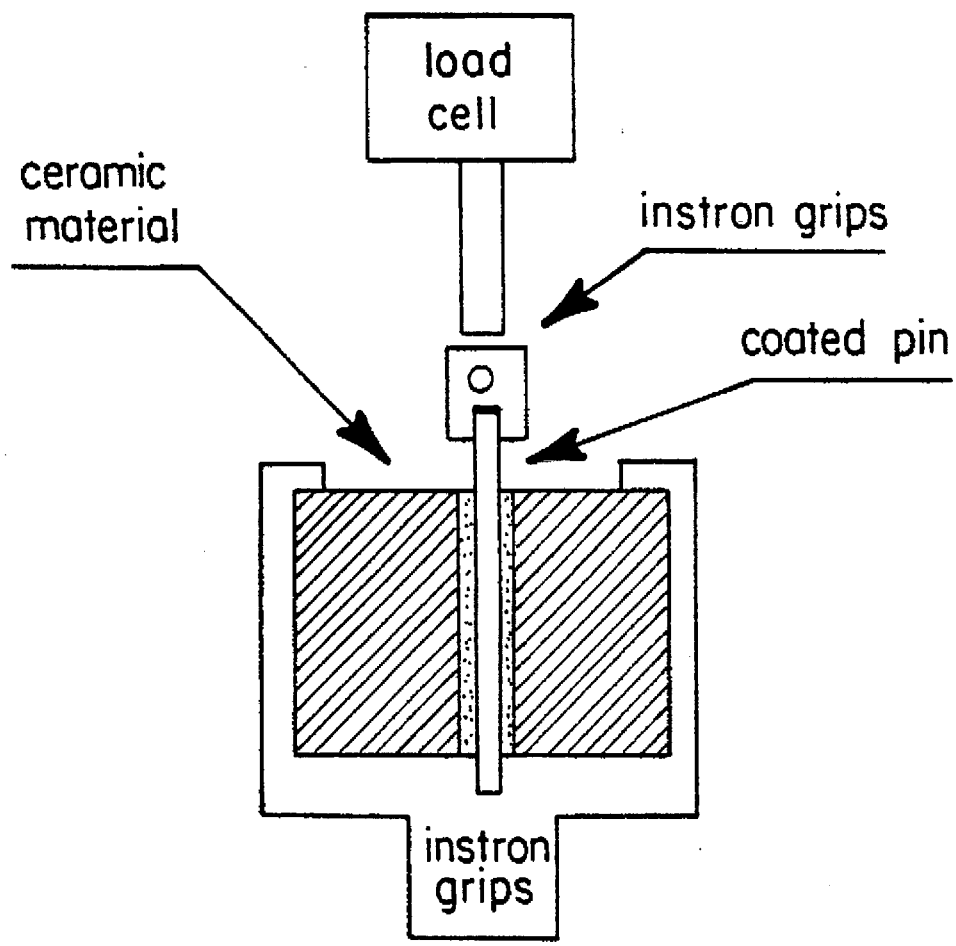
FIG. 1 is a schematic diagram showing the Instron testing device used to perform the pull out tests described herein.

The coated pins so obtained were placed in holes of the same diameter, 3.5, 4.5, 5.5, and 6.5 mm, drilled through a plaque of a ceramic material with a porosity similar to that of bone. The system (plaque and coated pin) was placed in distilled water at 37° C. for 3 days, after which the force necessary to pull the pin out from the plaque was measured. The pull out tests were performed on a Instron testing machine, model 4204, and comprised pulling the pin out from the cortical bone as shown in FIG. 1.

Figure 2:
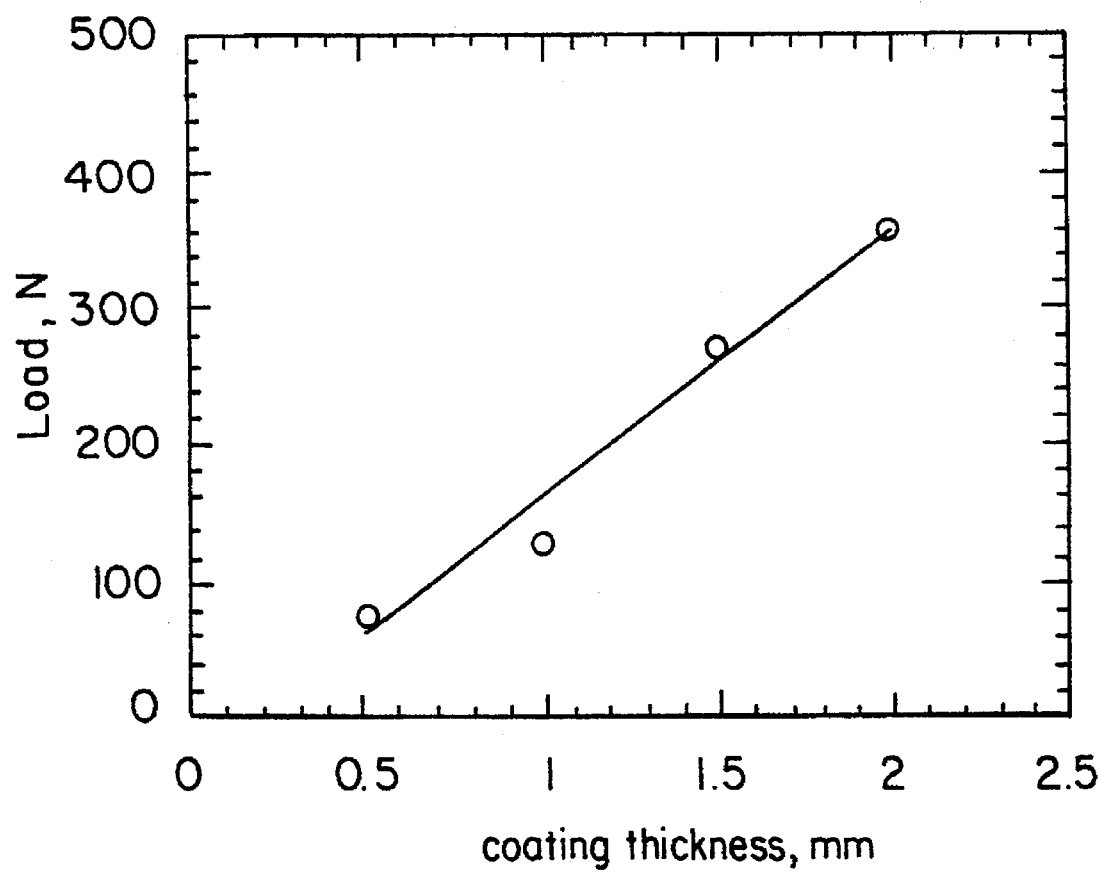
FIG. 2 is a graph showing the relationship between the coating thickness in mm and the load, N, necessary to pull the pins out from the plaque as described in Example 1.

The peak force to failure measured ranged from 80 Newtons for the 0.5 mm coating thickness of 330 Newtons for the 2 mm coating thickness, as shown in FIG. 2.

A similar test was performed by inserting a coated pin into the intramedullary cavity of a rabbit femur, and comparable results were obtained.

Furthermore, the stability of the nail-coating-bone system was tested by inserting the nail thus prepared in the intramedullary cavity and exposing it to various load cycles simulating the physiological fatigue which the system would have to undergo under normal conditions. The cycling load varied from −80 to +80 Newtons with different frequencies ranging from 0.4 to 10 Hertz. After almost 1,000 cycles, the pull out force was measured again. Almost the same value of the pull-out force was recorded for the sample before and after the load cycling, thus demonstrating the good mechanical stability of the system.

EXAMPLE 2

Figure 3A:
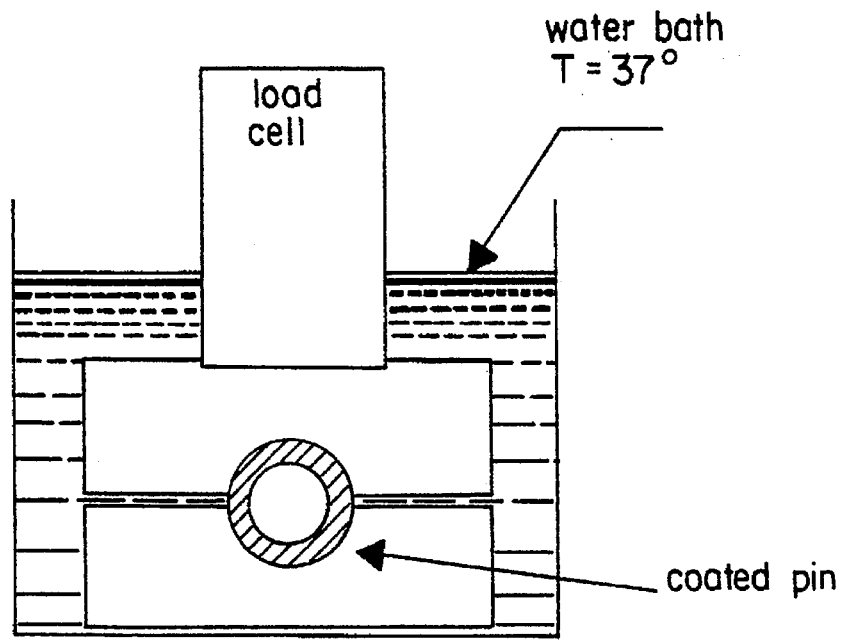
FIG. 3A shows the experimental apparatus employed to measure the load transmitted to the upper block during water absorption by the hydrogel, as described in Example 2.

Via the same procedure described in Example 1, stainless steel coated pins with coating thicknesses of 1 and 1.5 mm were obtained. With the aim of evaluating the time necessary to reach the maximum swelling stress, a compression stress relaxation test was performed by inserting the coated pins into two drilled marble blocks. The system (marble blocks—inserted pin) was placed in distilled water at 37° C. The load transmitted to the upper block during the water absorption was measured by means of an Instron dynamometer (FIG. 3A).

Figure 3B:
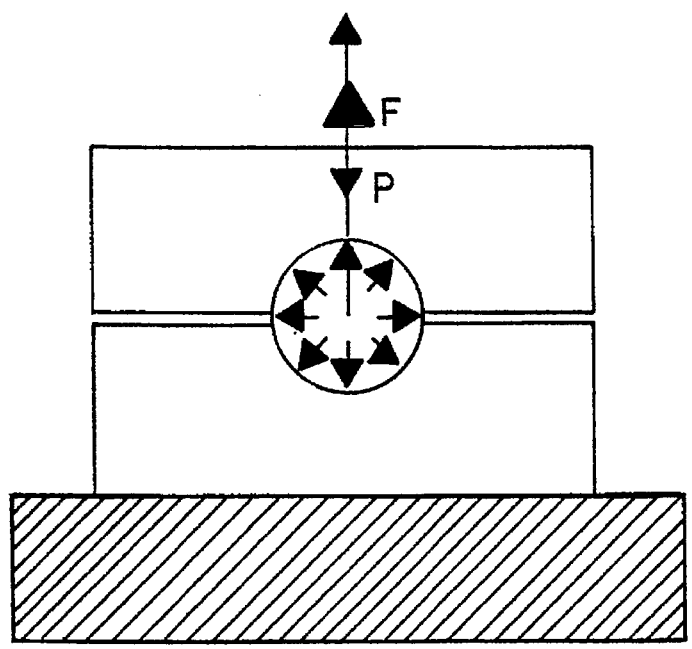
FIG. 3B is a schematic diagram showing how the stress in the hydrogel of Example 2 caused by water absorption is calculated by employing a force balance.

The stress in the hydrogel caused by water absorption was calculated using a force balance. The force F (recorded in the relaxation test in compression by the Instron apparatus) is the resultant of the force exerted by the PHEMA while absorbing water (FIG. 3A) minus the weight P of the upper part support (FIG. 3B).

Resolving the single interfacial stress component, S, vertically and integrating it, it is possible to calculate the resultant force (F):

$$F = S \cdot D \cdot L$$

where S is the interfacial stress and D and L are the diameter and length of the PHEMA coating, respectively. Since the system is immersed in water, the weight of the upper part support is given by:

$$W = V \cdot (dm - dw) \cdot g$$

where V is the volume of the upper part support, dm and dw are support and water density, respectively, and g is the gravitational acceleration.

Therefore, the swelling stress may be calculated from:

$$S = F - W/DL$$

Figure 4:
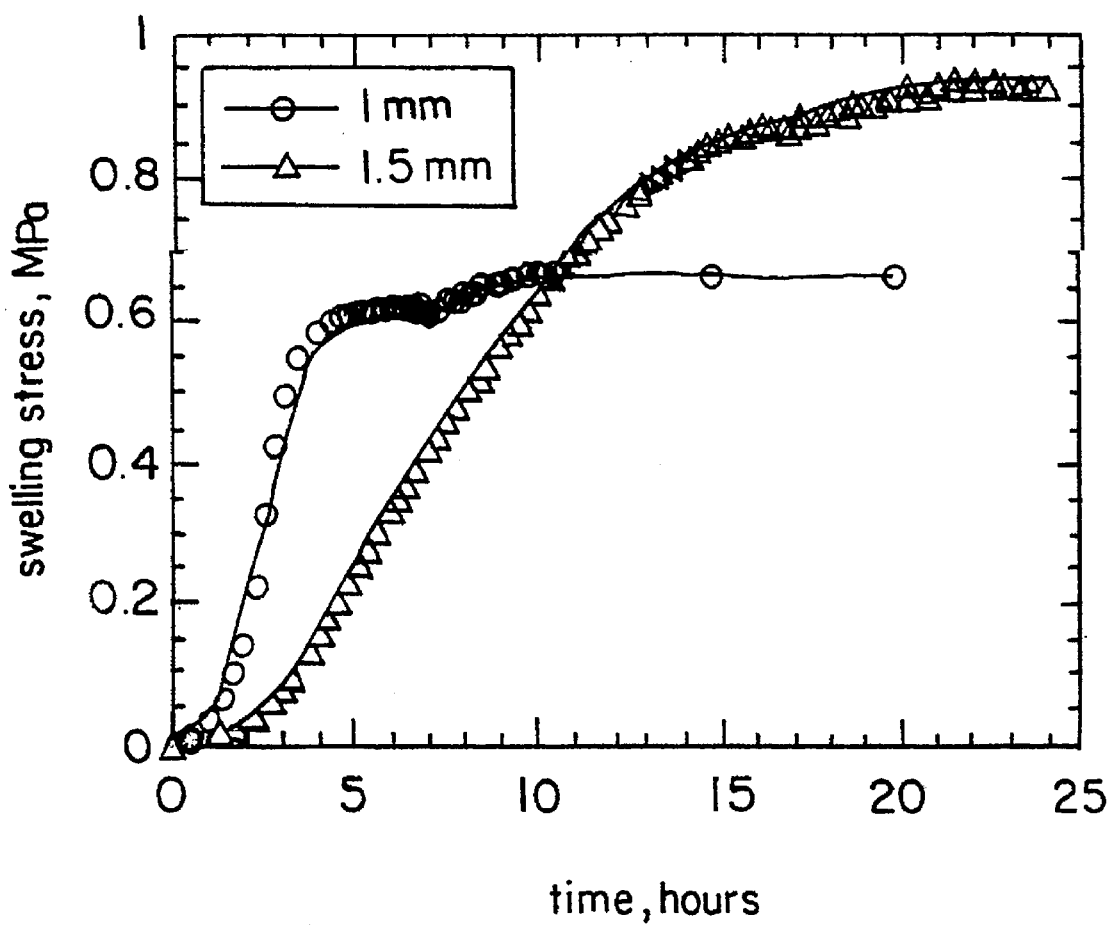
FIG. 4 is a graph showing the relationship between swelling stress, S, and time, generated during water absorption in Example 2.

The stress generated during water absorption, referred to as swelling stress, S, is plotted as a function of time in FIG. 4. For a coating thickness of 1.5 mm, an equilibrium swelling pressure of 0.93 MPa was achieved after approximately 20 hours. However, for the thinner coating thickness of 1 mm, this was considerably sooner, reaching a final stress value of 0.62 MPa after 7 hours. These values are far from the average cortical bone strength.

EXAMPLE 3

Employing the same coating procedure described in Example 1, stainless steel ware 2.5 mm in diameter was coated using a semi-interpenetrating polymer network (semi-IPN's) composed of crosslinked poly(2-hydroxyethylmethacrylate) (PHEMA) and poly (caprolactone) (PCL). The PHEMA/PCL blend had a composition of 90/10 by weight, and was prepared following the procedure described by P. A. Davis et al. (Poly(2-hydroxyethylmethacrylate) /poly(caprolactone) semi-interpenetrating polymer networks, *J. Bioactive and Compatible Polymers*, 3:205–218, 1988). Coated pins 30 mm in length and of four different external diameters, 3.5, 4.5, 5.5 and 6.5 mm, were inserted in ceramic plaques drilled with holes the same diameter as that of the pins. The system plaques and inserted pins were soaked in distilled water for 48 hours, after which the pull out force was evaluated. The results are shown in FIG. 5.

Figure 5:
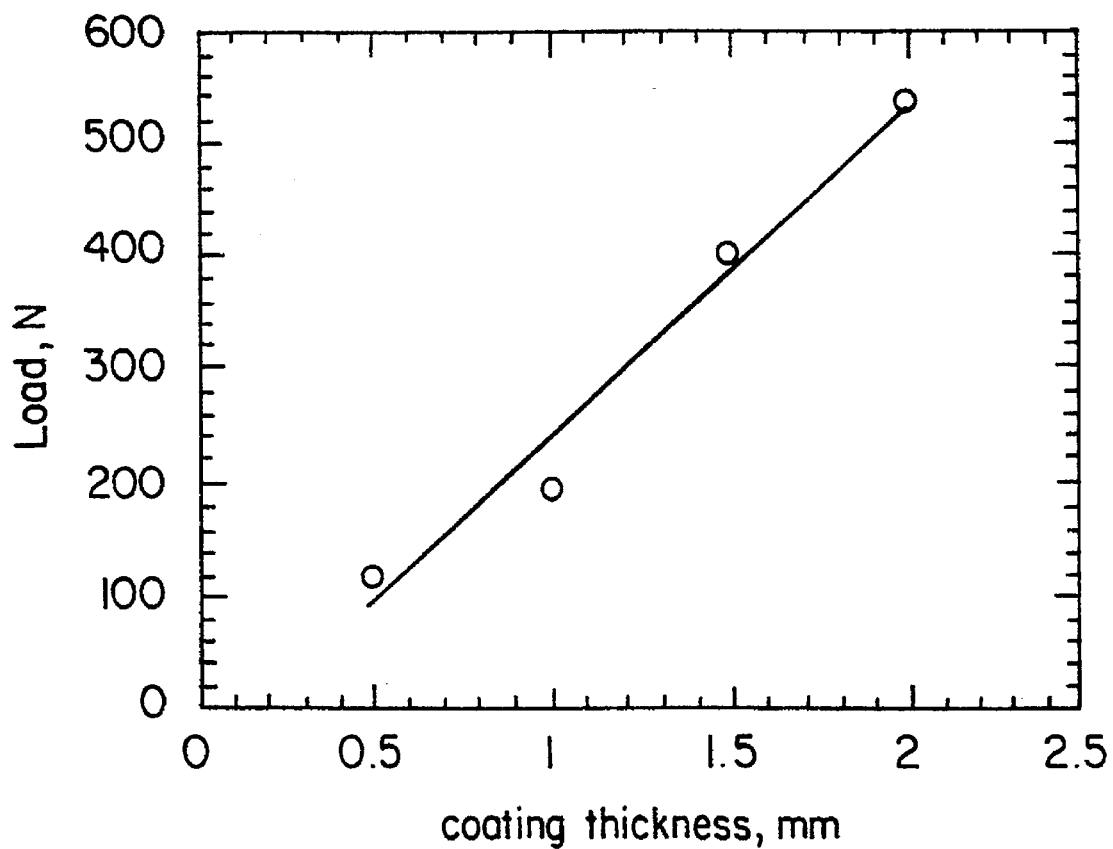
FIG. 5 is a graph showing the relationship between the coating thickness in mm and the load, N, necessary to pull the pins out from the plaque as described in Example 3.

As can be seen comparing FIG. 5 with FIG. 2, a notable increase in pull out force results when 10% of PCL is added to PHEMA. A wide variety of mechanical performances can be obtained by varying PCL compositions in the mixture. Since the inclusion of PCL in the PHEMA network leads to a decrease in the swelling power of the blend, the maximum pull out load, and hence the highest stability of the system, can be obtained by a suitable balance between the hydrophilic and the hydrophobic groups of the two constituents.

As reported by Davis et al., incorporation of biocompatible and biodegradable PCL into PHEMA hydrogels, besides improving the mechanical properties, allows natural tissue ingrowth since PCL degrades, leaving voids in the polymer matrix. In this way, the coating can be partially substituted by natural tissues, and the implant firmly anchored in the body.

EXAMPLE 4

Many ways exist to modify the mechanical properties of hydrogels in the swollen state and hence the level of the swelling stress exerted by the coating on the surrounding cortical bone. With the aim of providing only a few examples, considered below are some experimental results reported in the literature.

Migliaresi et al. (Water Sorption and Mechanical Properties of 2-Hydroxyethyl-Methacrylate and Methyl-Methacrylate Copolymers, *J. Biom. Mater. Res.*, 17, 1983) have reported that it is possible to obtain hydrogels with a wide range of mechanical behavior by copolymerization of 2-hydroxyethyl methacrylate (HEMA) and methyl-methacrylate (MMA). With a composition of 50% HEMA/MMA (w/w), they obtained a hydrogel with an elastic modulus 1,000 times higher than that exhibited by PHEMA alone, and with a water sorption capacity of about 20% (weight water/weight of dry polymer) against the 10% exhibited by PHEMA. From these data, assuming a linear relationship between the modulus and the degree of swelling with the pull out force, an increase of two orders of magnitude in the pull out force with this system to respect PHEMA is predicted.

Filling the hydrogel matrix with rigid organic or inorganic fillers like glass beads or hydroxyapatite crystals can greatly improve the mechanical properties, as reported by Nicolais et al. (Mechanical Behavior of Poly (2-Hydroxyethylmethacrylate) glass bead composites, *Chemistry and Properties of Crosslinked Polymers*, S. S. Labana, ed., Academic Press, Inc., 1977).

In this case, the mechanical properties, for example the elastic modulus, of the composite increase according to a linear relation:

$$Ec = Ef + (Eg - Ef)\phi g$$

where Ec, Ef, and Eg are the elastic moduli of the composite, filler, and gel, respectively, while $\phi g$ is the volume fraction of the gel in the composite.

Conversely, the degree of swelling decreases according to the equation:

$$SWc = \phi g SWg$$

where SWc and SWg are the degree of swelling of the composite and the gel, respectively.

As can be easily seen from the above equations, if Ef is much greater than Eg (as in the case of glass beads or hydroxyapatite crystals), it is possible to obtain a considerable increase in the elastic modulus, and hence in the swelling stress, without a drastic decrease in the swelling properties of the material.

Using the equation presented above, it is possible to design a coating material with swelling and mechanical properties suitable for any particular application.

EXAMPLE 5

Surgical titanium ware 2 mm in diameter was cut into 30 mm long pins. Before hydrogel coating, the pins were coated with a linear PMMA (polymethyl-methacrylate). The first coating was performed by dipping the titanium ping in a 40% by weight solution of PMMA in THF (tetrahydrofuran). After 10 dipping cycles, the PMMA coating thickness was about 0.5 mm. The pins thus obtained were subsequently coated with hydrogel following the same procedure described in Example 1. After the polymerization, the pins were placed in distilled water at 40° C. After 48 hours of immersion, the interfacial strength was measured by means of an Instron dynamometer, and proved to be close to the shear strength of the hydrogel in the swollen state (i.e., 3 MPa).

This result proves that it is possible to improve the interface adhesion, and hence the coating stability, between a hydrogel and any material by a previous coating with a non-swelling polymer which possesses groups chemically and/or physically related to those of the hydrogel.

EXAMPLE 6

Hydrogels are well known in the literature as drug carriers (*Hydrogels in Medicine and Pharmacy*, Vols. I, II and III, N. A. Peppas, ed., CRC Press Inc., Boca Raton, Fla., 1987). They can be filled with any pharmacologically active substance thanks to their high solubility in the swollen state.

A pharmacologically active coated pin can be produced following the same procedure described in Example 1. After the polymerization, the coating hydrogel is in the dry state. It can be filled with drug by soaking it in a solution containing a drug. After equilibrium has been reached, the pin can be removed from the solution and allowed to dry. After evaporation of the solvent, the drug will be trapped in the hydrogel network. When the pin thus prepared is placed into the intramedullary canal, the organic liquid will penetrate the hydrogel, allowing the diffusion of the drug into the body. This technique can be employed to avoid the antibiotic therapy that always follows such operations.

EXAMPLE 7

Other hydrogel coating materials useful in the present invention include the hyaluronic acid (HY) esters described in Examples 1–26 of PCT Patent Publication No. WO 92/13579. These include: the partial propyl ester of HY (50% esterified carboxylic groups, 50% salified carboxylic groups (Na)); the partial isopropyl ester of HY (50% esterified carboxylic groups, 50% salified carboxylic groups (Na)); the partial ethyl ester of HY (75% esterified carboxylic groups, 25% salified carboxylic groups (Na)); the partial methyl ester of HY (75% esterified carboxylic groups, 25% salified carboxylic groups (Na)); the methyl ester of HY; the ethyl ester of HY; the propyl ester of HY; the partial butyl ester of HY (50% esterified carboxylic groups, 50% salified carboxylic groups (Na)); the partial ethoxy-carbonylmethyl ester of HY (75% esterified carboxylic groups, 25% salified carboxylic groups (Na)); the n-pentyl ester of HY; the isopentyl ester of HY; the benzyl ester of HY; the β-phenylethyl ester of HY; the benzyl ester of HY; the partial propyl ester of HY (85% esterified carboxylic groups, 15% salified carboxylic groups (Na)); the n-octyl ester of HY; the isopropyl ester of HY; the 2,6-dichlorobenzyl ester of HY; the 4-terbutylbenzyl ester of HY; the heptadecyl ester of HY; the octadecyl ester of HY; the 3-phenylpropyl ester of HY; the 3,4,5-trimethoxy-benzyl ester of HY; the cinnamyl ester of HY; the decyl ester of HY; and the nonyl ester of HY.

EXAMPLE 8

Further hydrogel coating materials useful in the present invention are cross-linked esters of hyaluronic acid resulting from the esterification of HY with polyhydric alcohols, as described in Examples 1–37 of U.S. Pat. No. 4,957,744. These include cross-linked esters having a percentage of the hyaluronic acid carboxyls esterified with a polyhydric alcohol, and having the remaining carboxyls salified and/or esterified with a monohydric alcohol as shown in Table 1.

This Table lists the various useful products, describing the number of carboxyls esterified with the specified polyhydric alcohol, and the number of carboxyls salified with sodium and/or esterified with the specified monohydric alcohol.

TABLE 1

PERCENTAGE COMPOSITION OF THE VARIOUS CROSS-LINKED PRODUCTS

| EXAMPLES No. | No. OF ESTERIFIED CARBOXYLS PER 100 WITH... | No. OF CROSS-LINKED CARBOXYLS PER 100 WITH... | No. CARBOXYLS SALIFIED WITH SODIUM PER 100 |
|---|---|---|---|
| 1 | 5/$CH_3$—$CH_2$— | 5/—$(CH_2)_3$— | 90 |
| 2 | 5/$CH_3$—$CH_2$— | 10/—$(CH_2)_3$— | 85 |
| 3 | 5/$CH_3$—$CH_2$— | 20/—$(CH_2)_3$— | 75 |
| 4 | 10/$CH_3$—$CH_2$— | 20/—$(CH_2)_3$— | 70 |
| 5 | 20/$CH_3$—$CH_2$— | 20/—$(CH_2)_3$— | 60 |
| 6 | 40/$CH_3$—$CH_2$— | 20/—$(CH_2)_3$— | 40 |
| 7 | 60/$CH_3$—$CH_2$— | 20/—$(CH_2)_3$— | 20 |
| 8 | 75/$CH_3$—$CH_2$— | 20/—$(CH_2)_3$— | 5 |
| 9 | 40/$CH_3$—$CH_2$— | 40/—$(CH_2)_3$— | 20 |
| 10 | 20/$CH_3$—$CH_2$— | 20/—$(CH_2)_4$— | 60 |
| 11 | 40/$CH_3$—$CH_2$— | 20/—$(CH_2)_4$— | 40 |
| 12 | 60/$CH_3$—$CH_2$— | 20/—$(CH_2)_4$— | 20 |
| 13 | 20/$CH_3$—$CH_2$— | 20/—$(CH_2)_6$— | 60 |
| 14 | 40/$CH_3$—$CH_2$— | 20/—$(CH_2)_6$— | 40 |
| 15 | 60/$CH_3$—$CH_2$— | 20/—$(CH_2)_6$— | 20 |
| 16 | 5/$CH_3$—$CH_2$— | 5/—$(CH_2)_8$— | 90 |
| 17 | 5/$CH_3$—$CH_2$— | 10/—$(CH_2)_8$— | 85 |
| 18 | 5/$CH_3$—$CH_2$— | 20/—$(CH_2)_8$— | 75 |
| 19 | 10/$CH_3$—$CH_2$— | 20/—$(CH_2)_8$— | 70 |
| 20 | 20/$CH_3$—$CH_2$— | 20/—$(CH_2)_8$— | 60 |
| 21 | 40/$CH_3$—$CH_2$— | 20/—$(CH_2)_8$— | 40 |
| 22 | 60/$CH_3$—$CH_2$— | 20/—$(CH_2)_8$— | 20 |
| 23 | 75/$CH_3$—$CH_2$— | 20/—$(CH_2)_8$— | 5 |
| 24 | 40/$CH_3$—$CH_2$— | 40/—$(CH_2)_8$— | 20 |
| 25 | 20/$CH_3$—$CH_2$— | 20/—$(CH_2)_{10}$— | 60 |
| 26 | 40/$CH_3$—$CH_2$— | 20/—$(CH_2)_{10}$— | 40 |
| 27 | 60/$CH_3$—$CH_2$— | 20/—$(CH_2)_{10}$— | 20 |
| 28 | 40/$CH_3$—$CH_2$— | 20/—$(CH_2$—O—$CH_2)$— | 40 |
| 29 | 20/O—$CH_2$— | 20/—$(CH_2)_8$— | 60 |
| 30 | 20/O—$CH_2$— | 20/—$(CH_2$—O—$CH_2)$— | 60 |
| 31 | — | 20/—$(CH_2)_3$— | 80 |
| 32 | — | 50/—$(CH_2)_3$— | 50 |
| 33 | — | 80/—$(CH_2)_3$— | 20 |
| 34 | — | 20/—$(CH_2)_4$— | 80 |
| 35 | — | 20/—$(CH_2)_6$— | 80 |
| 36 | — | 20/—$(CH_2)_8$— | 80 |
| 37 | — | 20/—$(CH_2)_{10}$— | 80 |

EXAMPLE 9

Examples of antibiotic substances useful for impregnating the hydrogels and biocompatible/biodegradable materials of the present invention include basic and non-basic antibiotics, for example aminoglucosidics, macrolides, tetracyclines, and peptides, such as for example gentamicin, neomycin, streptomycin, dihydrostreptomycin, kanamycin, amikacin, tobramycin, spectinomycin, erythromycin, oleandomycin, carbomycin, spiramycin, oxytetracycline, rolitetracycline, bacitracin, polymyxin B, gramicidin, coilstin, chloramphenicol, thiamphenicol, lincomycin, vancomycin, novobiocin, ristocetin, clindamycin, amphotericin B, griseofulvin, nystatin and possibly their salts, such as sulfates or nitrates, or associations between the same or with other active principles, such as those mentioned hereafter.

Other drugs which can be used to advantage according to the present invention are: other anti-infective agents such as diethylcarbamazine, mebendazole, the sulfamides such as sulfacetamide, sulfadiazine, and sulfisoxazole; antiviral agents such as iododeoxyuridine, adenine arabinoside, trifluorothymidine, acyclovir, ethyldeoxyuridine, bromovinyldeoxyuridine, and 5-iodo-5'-amino-2', 5'-dideoxyuridine.

Of the antibiotics, the following are of particular note: erythromycin, bacitracin, gentamicin, neomycin, aureomycin, gramicidin and their associations; of the anti-bacterials and disinfectants: nitrofurazone, mafenids, chlorhexidine, and derivatives of 8-hydroxyquinoline and possibly their salts. This list is of course only for illustrative purposes, and any other antibiotic agents known or described in literature may be used.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. An orthopedic fastener or replacement, covered with a second coating comprising a hydrogel or other biocompatible, biodegradable material which expands in the presence of a liquid, wherein said hydrogel or other biocompatible, biodegradable material is a member selected from the group consisting of polyhydroxyethylmethacrylate, a semi-interpenetrating polymer network composed of crosslinked poly(2-hydroxyethylmethacrylate) and poly (caprolactone), a copolymer of 2-hydroxyethylmethacrylate and methylmethacrylate, poly(2-hydroxyethylmethacrylate), a hyaluronic acid ester, and a crosslinked ester of hyaluronic acid resulting from the esterification of hyaluronic acid with polyhydric alcohols; and wherein said fastener or replacement is first coated with a first coating of a non-swelling polymer possessing groups chemically and/or physically related to those of said hydrogel or said biocompatible, biodegradable material before coating said fastener or replacement with either said hydrogel or said biocompatible, biodegradable material.

2. The orthopedic fastener or replacement of claim 1, wherein said fastener or replacement is in the form selected from the group consisting of a nail, a screw, a pin, a hip replacement, a knee replacement, and an angle replacement.

3. The orthopedic fastener or replacement of claim 1, wherein said hydrogel or other biocompatible, biodegradable material possesses hydrophilic and hydrophobic groups in its polymeric network.

4. The orthopedic fastener or replacement of claim 1, wherein said fastener or replacement is made of stainless steel, a metal alloy, titanium, or cobalt-chromium.

5. The orthopedic fastener or replacement of claim 1, wherein said second coating is formed from a crosslinked material and wherein the degree of crosslinking of said second coating is controlled by the temperature at which polymerization is conducted.

6. The orthopedic fastener or replacement of claim 1, wherein unreacted monomers are removed from said second coating by immersing the coated fastener or replacement in water.

7. The orthopedic fastener or replacement of claim 1, wherein said poly(2-hydroxyethylmethacrylate) and said poly(caprolactone) are present in said second coating in a ratio of 90:10, w/w.

8. The orthopedic fastener or replacement of claim 1, wherein the mechanical performance of said crosslinked poly(2-hydroxyethylmethacrylate) and said poly(caprolactone) in said second coating is varied by varying the amount of poly(caprolactone) in the mixture.

9. The orthopedic fastener or replacement of claim 1, wherein said 2-hydroxyethylmethacrylate and said methylmethacrylate are present in said second coating in a ratio of 50:50, w/w.

10. The orthopedic fastener or replacement of claim 1, wherein the second coating has a thickness in the range of from about 0.5 mm to 2 mm.

11. The orthopedic fastener or replacement of claim 1, wherein said hydrogel or other biocompatible, biodegradable material in said second coating further comprises a rigid organic or inorganic filler.

12. The orthopedic fastener or replacement of claim 11, wherein said rigid inorganic filler is a member selected from the group consisting of glass beads and hydroxyapatite crystals.

13. The orthopedic fastener or replacement of claim 1, wherein said poly(2-hydroxyethylmethacrylate) further comprises glass bead composites.

14. The orthopedic fastener or replacement of claim 1, wherein said non-swelling polymer is linear polymethylmethacrylate.

15. The orthopedic fastener or replacement of claim 1, wherein said hydrogel or other biocompatible, biodegradable material is impregnated with at least one pharmacologically active substance.

16. The orthopedic fastener or replacement of claim 15, wherein said pharmacologically active substance is at least one member selected from the group consisting of an antibiotic, an antiviral agent, an anti-infective agent, an antibacterial agent, and a disinfectant.

17. The orthopedic fastener or replacement of claim 16, wherein said antibiotic is at least one member selected from the group consisting of an aminoglucoside, a macrolide, a tetracycline, and a peptide.

18. The orthopedic fastener or replacement of claim 16, wherein said antibiotic is at least one member selected from the group consisting of gentamicin, neomycin, streptomycin, dihydrostreptomycin, kanamycin, amikacin, tobramycin, spectinomycin, erythromycin, aureomycin, oleandomycin, carbomycin, spiramycin, oxytetracycline, rolitetracycline, bacitracin, polymyxin B, gramicidin, colistin, chloramphenicol, thiamphenicol, lincomycin, vancomycin, novobiocin, ristocetin, clindamycin, amphotericin B, griseofulvin, nystatin, and a physiologically acceptable salt thereof.

19. The orthophedic fastener or replacement of claim 16, wherein said antiviral agent is at least one member selected from the group consisting of iododeoxyuridine, adenine arabinoside, trifluorothymidine, acyclovir, ethyldeoxyuridine, bromovinyldeoxyuridine, and 5-iodo-5'-amino-2', 5'-dideoxyuridine.

20. The orthopedic fastener or replacement of claim 16, wherein said anti-infective agent is at least one member selected from the group consisting of diethylcarbamazine, mebendazole, and a sulfamide.

21. The orthopedic fastener or replacement of claim 16, wherein said antibacterial is at least one member selected from the group consisting of nitrofurazone, mafenids, chlorhexidine, and a derivative of 8-hydroxyquinoline.

22. The orthopedic fastener or replacement of claim 1, wherein said hyaluronic acid ester is at least one member selected from the group consisting of the partial propyl ester of hyaluronic acid (HY) having 50% esterified carboxylic groups, and 50% sodium salified carboxylic groups; the partial isopropyl ester of HY having 50% esterified carboxylic groups, and 50% sodium salified carboxylic groups; the partial ethyl ester of HY having 75% esterified carboxylic groups, and 25% sodium salified carboxylic groups; the partial methyl ester of HY having 75% esterified carboxylic groups, and 25% sodium salified carboxylic groups; the methyl ester of HY; the ethyl ester of HY; the propyl ester of HY; the partial butyl ester of HY having 50% esterified carboxylic groups, and 50% sodium salified carboxylic groups; the partial ethoxycarbonylmethyl ester of HY having 75% esterified carboxylic groups, and 25% sodium salified carboxylic groups the n-pentyl ester of HY; the isopentyl ester of HY; the benzyl ester of HY; the β-phenylethyl ester of HY; the benzyl ester of HY; the partial propyl ester of HY having 85% esterified carboxylic groups, and 15% sodium salified carboxylic groups the n-octyl ester of HY; the isopropyl ester of HY; the 2,6-dichlorobenzyl ester of HY; the 4-[terbutylbenzyl] tertbutylbenzyl ester of HY; the heptadecyl ester of HY; the octadecyl ester of HY; the 3-phenylpropyl ester of HY; the 3,4,5-trimethoxybenzyl ester of HY; the cinnamyl ester of HY; the decyl ester of HY; and the nonyl ester of HY.

23. The orthopedic fastener or replacement of claim 1, wherein said crosslinked ester of hyaluronic acid is at least one member selected from the group consisting of the crosslinked esters listed in the following Table

TABLE 1

| PERCENTAGE COMPOSITION OF THE VARIOUS CROSS-LINKED PRODUCTS | | |
|---|---|---|
| EXAMPLES No. | No. OF ESTERIFIED CARBOXYLS PER 100 WITH... | No. OF CROSS-LINKED CARBOXYLS PER 100 WITH... | No. CARBOXYLS SALIFIED WITH SODIUM PER 100 |
| 1 | 5/$CH_3$—$CH_2$— | 5/—$(CH_2)_3$— | 90 |
| 2 | 5/$CH_3$—$CH_2$— | 10/—$(CH_2)_3$— | 85 |
| 3 | 5/$CH_3$—$CH_2$— | 20/—$(CH_2)_3$— | 75 |
| 4 | 10/$CH_3$—$CH_2$— | 20/—$(CH_2)_3$— | 70 |
| 5 | 20/$CH_3$—$CH_2$— | 20/—$(CH_2)_3$— | 60 |
| 6 | 40/$CH_3$—$CH_2$— | 20/—$(CH_2)_3$— | 40 |
| 7 | 60/$CH_3$—$CH_2$— | 20/—$(CH_2)_3$— | 20 |
| 8 | 75/$CH_3$—$CH_2$— | 20/—$(CH_2)_3$— | 5 |
| 9 | 40/$CH_3$—$CH_2$— | 40/—$(CH_2)_3$— | 20 |
| 10 | 20/$CH_3$—$CH_2$— | 20/—$(CH_2)_4$— | 60 |
| 11 | 40/$CH_3$—$CH_2$— | 20/—$(CH_2)_4$— | 40 |
| 12 | 60/$CH_3$—$CH_2$— | 20/—$(CH_2)_4$— | 20 |
| 13 | 20/$CH_3$—$CH_2$— | 20/—$(CH_2)_6$— | 60 |
| 14 | 40/$CH_3$—$CH_2$— | 20/—$(CH_2)_6$— | 40 |
| 15 | 60/$CH_3$—$CH_2$— | 20/—$(CH_2)_6$— | 20 |
| 16 | 5/$CH_3$—$CH_2$— | 5/—$(CH_2)_8$— | 90 |
| 17 | 5/$CH_3$—$CH_2$— | 10/—$(CH_2)_8$— | 85 |

TABLE 1-continued

PERCENTAGE COMPOSITION OF THE
VARIOUS CROSS-LINKED PRODUCTS

| EXAMPLES No. | No. OF ESTERIFIED CARBOXYLS PER 100 WITH... | No. OF CROSS-LINKED CARBOXYLS PER 100 WITH... | No. CARBOXYLS SALIFIED WITH SODIUM PER 100 |
|---|---|---|---|
| 18 | 5/CH$_3$—CH$_2$— | 20/—(CH$_2$)$_8$— | 75 |
| 19 | 10/CH$_3$—CH$_2$— | 20/—(CH$_2$)$_8$— | 70 |
| 20 | 20/CH$_3$—CH$_2$— | 20/—(CH$_2$)$_8$— | 60 |
| 21 | 40/CH$_3$—CH$_2$— | 20/—(CH$_2$)$_8$— | 40 |
| 22 | 60/CH$_3$—CH$_2$— | 20/—(CH$_2$)$_8$— | 20 |
| 23 | 75/CH$_3$—CH$_2$— | 20/—(CH$_2$)$_8$— | 5 |
| 24 | 40/CH$_3$—CH$_2$— | 40/—(CH$_2$)$_8$— | 20 |
| 25 | 20/CH$_3$—CH$_2$— | 20/—(CH$_2$)$_{10}$— | 60 |
| 26 | 40/CH$_3$—CH$_2$— | 20/—(CH$_2$)$_{10}$— | 40 |
| 27 | 60/CH$_3$—CH$_2$— | 20/—(CH$_2$)$_{10}$— | 20 |
| 28 | 40/CH$_3$—CH$_2$— | 20/—(CH$_2$—O—CH$_2$)— | 40 |
| 29 | 20/O—CH$_2$— | 20/—(CH$_2$)$_8$— | 60 |
| 30 | 20/O—CH$_2$— | 20/—(CH$_2$—O—CH$_2$)— | 60 |
| 31 | — | 20/—(CH$_2$)$_3$— | 80 |
| 32 | — | 50/—(CH$_2$)$_3$— | 50 |
| 33 | — | 80/—(CH$_2$)$_3$— | 20 |
| 34 | — | 20/—(CH$_2$)$_4$— | 80 |
| 35 | — | 20/—(CH$_2$)$_6$— | 80 |
| 36 | — | 20/—(CH$_2$)$_8$— | 80 |
| 37 | — | 20/—(CH$_2$)$_{10}$— | 80 |

24. A method for fixing a bone or bone replacement in position, comprising the steps of:
(a) providing a hole in existing bone to accommodate a fastener;
(b) locating a bone or bone replacement adjacent to said existing bone, said bone or bone replacement having a hole therein to accommodate a fastener;
(c) providing an orthopedic fastener or replacement, covered with a second coating comprising a hydrogel or other biocompatible, biodegradable material which expands in the presence of a liquid, wherein said hydrogel or other biocompatible, biodegradable material is a member selected from the group consisting of polyhydroxyethylmethacrylate, a semi-interpenetrating polymer network composed of crosslinked poly(2-hydroxyethylmethacrylate) and poly(caprolactone), a copolymer of 2-hydroxyethylmethacrylate and methylmethacrylate, poly(2-hydroxyethylmethacrylate), a hyaluronic acid ester, and a crosslinked ester of hyaluronic acid resulting from the esterification of hyaluronic acid with polyhydric alcohols; and wherein said fastener or replacement is first coated with a first coating of a non-swelling polymer possessing groups chemically and/or physically related to those of said hydrogel or said biocompatible, biodegradable material before coating said fastener or replacement with either said hydrogel or said biocompatible, biodegradable material; and (d) inserting said fastener of step (c) into the holes in said existing bone and said bone or bone replacement such that said coating absorbs fluid and swells, thereby securely fixing said bone or bone replacement in position.

25. The method of claim 24, wherein the secure fixing of step (d) is accomplished by the swelling of said coating to fill gaps between said fastener and said existing bone, and between said fastener and said bone or bone replacement.

26. The orthopedic fastener or replacement of claim 1, wherein said fastener or replacement is in the form selected from the group consisting of an intramedullar nail, a spiral screw, and an intracortical screw.

* * * * *